United States Patent
Yuan et al.

(10) Patent No.: US 12,031,969 B2
(45) Date of Patent: Jul. 9, 2024

(54) SPATIAL AND TEMPORAL FEATURE-BASED METHOD FOR MEASURING DOMESTIC WASTEWATER EFFLUENT LOADINGS

(71) Applicant: Nanjing University, Nanjing (CN)

(72) Inventors: Zengwei Yuan, Nanjing (CN); Xin Liu, Nanjing (CN)

(73) Assignee: Nanjing University, Nanjing (CN)

( * ) Notice: Subject to any disclaimer, the term of this patent is extended or adjusted under 35 U.S.C. 154(b) by 727 days.

(21) Appl. No.: 17/114,527

(22) Filed: Dec. 8, 2020

(65) Prior Publication Data

US 2022/0178902 A1    Jun. 9, 2022

(51) Int. Cl.
| | |
|---|---|
| G01N 33/18 | (2006.01) |
| C02F 1/00 | (2023.01) |
| G01N 1/20 | (2006.01) |
| G01N 27/06 | (2006.01) |

(52) U.S. Cl.
CPC .............. G01N 33/18 (2013.01); C02F 1/008 (2013.01); G01N 1/20 (2013.01); C02F 2209/08 (2013.01); C02F 2209/14 (2013.01); C02F 2209/40 (2013.01); G01N 1/2035 (2013.01); G01N 27/06 (2013.01)

(58) Field of Classification Search
USPC ........................................................ 702/25
See application file for complete search history.

(56) References Cited

U.S. PATENT DOCUMENTS

| | | | |
|---|---|---|---|
| 2003/0230523 A1* | 12/2003 | Polizzotto .............. | G06Q 10/00 210/143 |
| 2020/0262726 A1* | 8/2020 | Munk-Nielsen ...... | C02F 1/5209 |
| 2020/0385297 A1* | 12/2020 | Liu ........................ | C02F 1/008 |

* cited by examiner

*Primary Examiner* — Paul D Lee
(74) *Attorney, Agent, or Firm* — Proi Intellectual Property US; Klaus Michael Schmid

(57) ABSTRACT

The invention discloses a spatial and temporal feature-based method for measuring domestic wastewater effluent loadings, comprising the following steps: establish a model for measuring regional domestic wastewater effluent loadings; calculate regional population distribution raster data; obtain per capita effluent loading coefficients with spatial and temporal differences; calculate regional domestic wastewater effluent loadings; and compare and analyze the temporal fluctuation features and spatial variation features of regional domestic wastewater effluent loadings and identify "hotspot" periods and areas of effluent loadings. Compared with the prior art, the method for measuring domestic wastewater effluent loadings provided by the present invention is flexible, convenient and highly universal, which can significantly raise the temporal-spatial resolution of the pattern of regional domestic wastewater effluent loadings. The data needed are also publicly available. This invention can help identify key pollution areas and periods and lay a methodological foundation for precision pollution control.

8 Claims, 1 Drawing Sheet

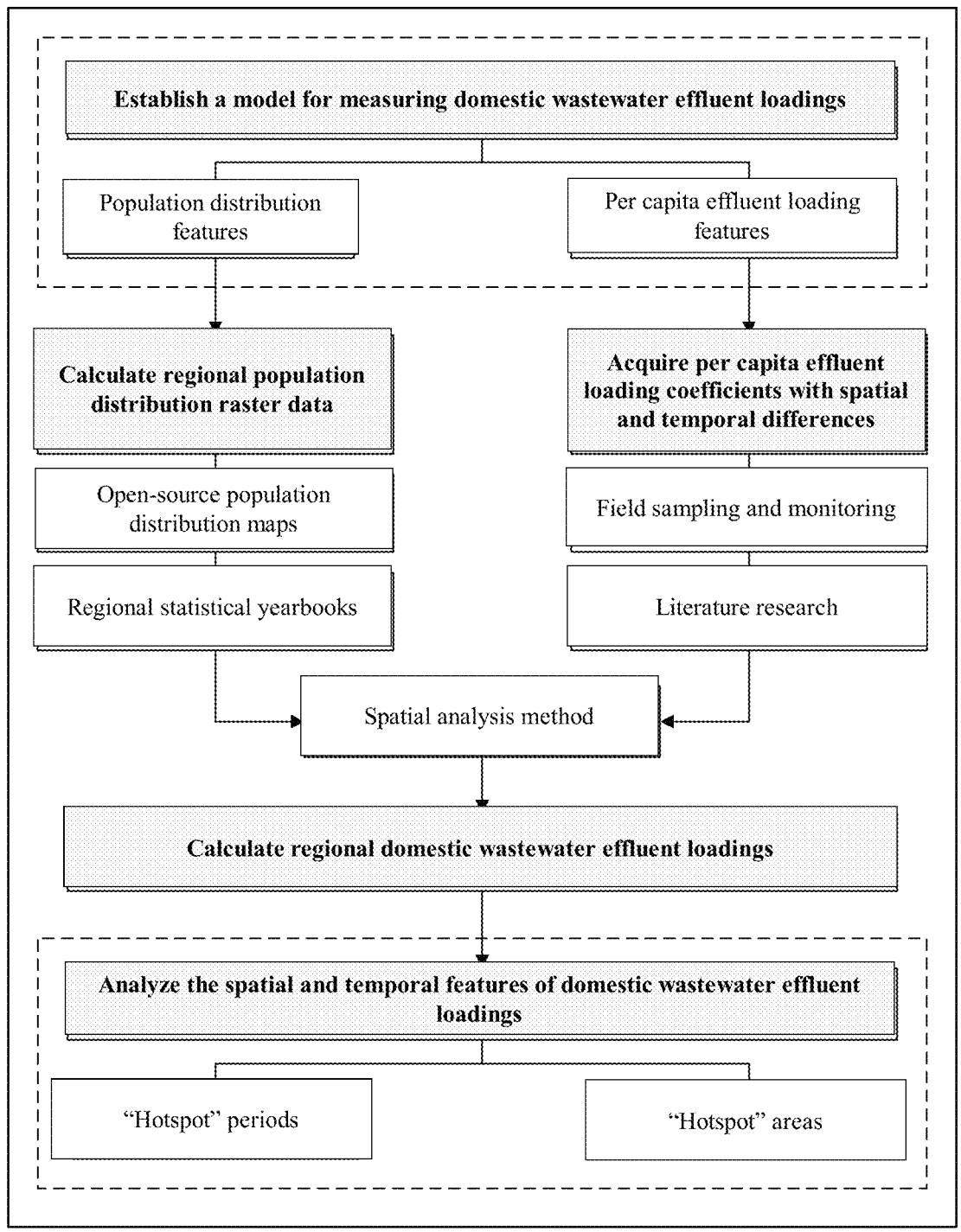

SPATIAL AND TEMPORAL FEATURE-BASED METHOD FOR MEASURING DOMESTIC WASTEWATER EFFLUENT LOADINGS

TECHNICAL FIELD

The present invention relates to the field of water pollution loading measurement, particularly to a spatial and temporal feature-based method for measuring domestic wastewater effluent loadings.

BACKGROUND ART

With the improvement of residents' living standards, domestic water consumption and domestic wastewater discharge are increasing. Due to the high pipe connection rate of domestic wastewater, its pollution reduction focuses on end treatment, and the importance of source prevention is often ignored. However, from the perspective of pollution loading generation, the proportion of domestic wastewater is increasing, and it has become a main source of water pollution loading in highly urbanized areas, and it is a key object of precision pollution control.

The pre-assessment of a conventional environmental protection project often adopts a measuring method based on the wastewater flow and pollutant concentration of a coastal discharge outlet. This method proceeds from the perspective of end treatment. Although it can determine the amount of pollution loading entering the water body, it cannot trace its upstream pollution sources. Examples: An integrated method for calculating the volume and loadings of low-pollution water in a lake basin disclosed by CN104217102A considers the tail water of wastewater treatment plants, rural farmland runoff, urban surface runoff volume and pollution loadings; CN107526880A patent measures the upstream pollution flux into the river based on the process observation data of water quality concentration in the downstream section of the river.

For a long time, pollution loadings have been measured mainly based on the needs of total amount accounting. Activity level data and wastewater effluent coefficients mostly directly use poorly time-sensitive macro statistics data. Spatial representation can be implemented to the administrative division level only and the temporal-spatial resolution is not high. Examples: CN108734401A patent developed a river pollution assessment method based on SPARROW Model, and the pollution level of domestic sources is calculated by multiplying the statistics data of pollution of domestic sources with the proportion of the population in each sub-basin to the population of the administrative district. CN108717453A patent developed a method for calculating pollution loading in a plain river network area based on a GIS platform. The amount of pollutants produced by residents is calculated by directly multiplying the population in a statistical yearbook with an efficient obtained from an urban domestic wastewater effluent loading coefficient manual of national pollution source census. CN107122620A patent provides a method for measuring exogenous phosphorus loading in a drainage basin. Although the method improves the spatial and temporal accuracy of domestic pollution loading measurement, it relies on big data of resident's water consumption, which is hardly available in general.

Therefore, it is a matter of realistic significance to establish a spatial and temporal feature-based method for measuring domestic wastewater effluent loadings to accurately identify "hotspot" periods and spatial distribution features of domestic wastewater effluent loading, thereby providing more detailed and concrete decision support for whole-process precision pollution control on a basin scale, guiding the orderly advancement of source control and pollution reduction measures according to circumstances and also providing a method and mechanism reference for water environment management and lake eutrophication control.

SUMMARY OF THE INVENTION

Object of the invention: An object of the present invention is to provide a spatial and temporal feature-based method for measuring domestic wastewater effluent loadings in view of the defects of the prior art to raise the spatial and temporal measurement accuracy of domestic wastewater effluent loadings and discriminate "hotspots" of domestic wastewater effluent loading, thereby leading the innovation in decision-making means and methods for water environment treatment.

Technical solution: The spatial and temporal feature-based method for measuring domestic wastewater effluent loadings provided by the present invention comprises the following steps:

Step 1. Establish a model for measuring regional domestic wastewater effluent loadings based on spatial and temporal differences in population distribution and per capita effluent loading features, under the basic principle of "effluent loadings=number of population×per capita daily consumption of domestic water×domestic wastewater effluent coefficient×pollutant concentration×number of days"; and for the purpose of identifying the spatial and temporal distribution features of effluent loadings, divide the measured region into a number of independent grids and set the size of the grids according to the required resolution to establish a spatial model for measuring regional domestic wastewater effluent loadings, including domestic wastewater effluent loadings of every grid divided in the region on a single working day, on a single rest day and in a whole year, respectively;

Step 2. Obtain regional population distribution raster data according to open-source population distribution databases, statistical yearbooks and spatial analytical methods;

Step 3. Obtain per capita effluent loading coefficients in the region based on field sampling and monitoring, and literature;

Step 4. Use the model for measuring regional domestic wastewater effluent loadings, the regional population distribution raster data and the per capita effluent loading coefficients in the region to calculate regional domestic wastewater effluent loadings in geographic information system software; and Step 5. Identify hotspot periods and hotspot areas of domestic wastewater effluent loadings.

As a further preferred technical solution of the present invention, the domestic wastewater effluent loadings at Step (1) refer to the amount of pollutants directly discharged from households to the outdoor after their water consumption and different from the reception amount of environmental media. The water users do not include public services such as administrative and institutional undertakings, operating services and special industries. The pollutants include chemical oxygen demand (COD), ammonia nitrogen ($NH_3$—N), total nitrogen (TN), and total phosphorus (TP).

Preferably, at Step 1, the following calculation formulae are used to calculate the domestic wastewater effluent loadings on a single working day, on a single rest day and in a whole year, respectively:

$$Q_{k,w}=p\times w\times f\times C_{w,n}\times 10^{-9}$$

$$Q_{k,r}=p\times w\times f\times C_{r,n}\times 10^{-9}$$

$$Q_k=Q_{k,w}\times d_w+Q_{k,r}\times d_r$$

where:

$Q_{k,w}$ and $Q_{k,r}$ are the domestic wastewater effluent loadings of grid k on a single working day and a single rest day, respectively, and the unit is t; $Q_k$ is the domestic wastewater effluent loadings of grid k in a whole year, and the unit is t; p is the population of grid k; w is the per capita daily consumption of domestic water, and the unit is L; f is the domestic wastewater effluent coefficient; and $C_{r,n}$ are the weighted average pollutant concentration of subdistrict n on working days and rest days, respectively, and the unit is mg/L; n is the subdistrict to which grid k belongs; and $d_w$ and $d_r$ are the number of working days and the number of rest days, respectively in a target year.

Preferably, at Step 2, the regional population distribution raster data are obtained by the following method:
(1) Download the recently published regional population distribution data map of a specific historical year from the open-source database;
(2) Use the regional administrative boundary layer to intercept the regional population distribution raster layer of the specific historical year to generate a regional population distribution map of the current year;
(3) Assume that the spatial distribution pattern of regional population remains stable in a short term, use the population data in the regional statistical yearbook to calculate the population conversion coefficient between a target year and the specific historical year, i.e., the population ratio between the two years;
(4) In the geographic information system software, multiply the regional population distribution raster layer of the specific historical year with the population conversion coefficient to obtain a regional population distribution raster layer of the target year; and
(5) In the geographic information system software, set the resolution of the regional population distribution raster layer.

Preferably, at Step 3, the per capita effluent loading coefficients include the per capita daily consumption of domestic water, the domestic wastewater effluent coefficient and the concentration of various pollutants. The per capita daily consumption of domestic water comes from regional statistical yearbooks or government work reports, the domestic wastewater effluent coefficient is obtained from literature, and the pollutant concentrations are obtained by means of field sampling and monitoring.

Preferably, pollutant concentrations are monitored by the following specific method:
(1) Select representative residential quarters for monitoring: In order to reflect the spatial representativeness of pollutant concentration sampling, a stratified sampling method is adopted. Taking China as an example, according to the Division Codes for Statistics and Urban and Rural Division Codes in 2018, the levels of administrative division in China from top to bottom is: administrative province, prefecture-level city, district/county, subdistrict/town, and community/administrative village. At the level of community/administrative village, considering urban and rural differences in development features, the whole region is divided into three categories including urban areas, suburban areas and rural areas; and take samples respectively. In each category, according to the sub-regional average housing price in the target year, the uniformity in spatial distribution and field pre-investigation, determine residential quarters for actual monitoring, which can represent the communities or administrative villages to which they belong;
(2) Continuous monitoring of residential quarters: Choose the general wastewater discharge outlet of each residential quarter as the sampling site to carry out continuous monitoring for the purpose of reflecting temporal fluctuations of pollutant concentration; set the sampling time to be on Friday and Saturday, which represent a working day and a rest day, respectively; and set the sampling interval to be once every 4 hours;
(3) Sample recording and storing: Before sampling, record the diameter of the wastewater discharge pipe and the longitude and latitude of the sampling site; record the time that wastewater discharge needs to fill up a 3.5 L water bucket and calculate the wastewater flow; and apply standard analytical methods to store the samples and test the concentration of pollutants;
(4) Calculate the weighted average pollutant concentration of each sampling quarter on a single working day and a single rest day, respectively, by the following formulae:

$$c_{w,m} = \frac{\sum_{i=1}^{6}(q_{w,i}\times c_{w,i})}{\sum_{i=1}^{6}q_{w,i}}$$

$$c_{r,m} = \frac{\sum_{i=1}^{6}(q_{r,i}\times c_{r,i})}{\sum_{i=1}^{6}q_{r,i}}$$

where:

$c_{w,m}$ and $c_{r,m}$ are the weighted average pollutant concentration of sampling quarter m on working days and rest days, respectively, and the unit is mg/L; i is the number of sampling intervals on a single working day or rest day; $q_{w,i}$ and $q_{r,i}$ are the wastewater flow in sampling interval i of working days and rest days, respectively, and the unit is L/s; and $c_{w,i}$ and $c_{r,i}$ are the pollutant concentration in sampling interval i of working days and rest days, respectively, and the unit is mg/L;
(5) The weighted average pollutant concentration of domestic wastewater in each subdistrict on a single working day and that on a single rest day are calculated by the following formulae:

$$C_{w,n} = \frac{N_a}{N_a+N_b+N_c}\times C_{w,c} + \frac{N_b}{N_a+N_b+N_c}\times C_{w,t} + \frac{N_c}{N_a+N_b+N_c}\times C_{w,r}$$

$$C_{r,n} = \frac{N_a}{N_a+N_b+N_c}\times C_{r,c} + \frac{N_b}{N_a+N_b+N_c}\times C_{r,t} + \frac{N_c}{N_a+N_b+N_c}\times C_{r,r}$$

where:

$C_{w,n}$ and $C_{r,n}$ are the weighted average pollutant concentration in subdistrict n on working days and rest days, respectively, and the unit is mg/L; $N_a$ is the number of communities, which are under the jurisdiction of subdistrict n and are divided into urban codes; $N_b$ is the number of communities, which are under the jurisdiction of subdistrict n and are divided into suburban codes; $N_c$ is the number of communities, which are under the jurisdiction of subdistrict n and are divided into rural codes; $C_{w,c}$ and $C_{r,c}$ are the weighted average pollutant concentration in the urban quarters of subdistrict n on working days and rest days, respectively and the unit is mg/L; $C_{w,t}$ and $C_{r,t}$ are the weighted average pollutant concentration in the suburban quarters of subdistrict n on working days and rest days, respectively, and the unit is mg/L; and $C_{w,r}$ and $C_{r,r}$ are the weighted average pollutant concentration in the rural quarters of subdistrict n on working days and rest days, respectively, and the unit is mg/L;

(6) In the geographic information system software, combine the information of the weighted average pollutant concentrations of domestic sources in each subdistrict in the region on working days and rest days with the vector diagram of the subdistrict based on the names of subdistricts to obtain the pollutant concentration distribution map of each subdistrict in the region.

Preferably, at Step 4, the regional domestic wastewater effluent loadings are calculated through the following specific steps:

(1) In the geographic information system software, convert the subdistrict vector layer that relates the pollutant concentration information into a raster layer, and set the resolution of the raster layer to be consistent with the resolution of the regional population distribution raster layer;

(2) In the geographic information system software, input the formula for calculating regional domestic wastewater effluent loadings, which are the product of the regional population distribution raster layer, the daily weighted average pollutant concentration distribution raster layer (subdistrict-specific) and other necessary parameters to obtain distribution maps of various pollutants on a single working day, on a single rest day and in a whole year.

Preferably, at Step 5, hotspot periods and hotspot areas of domestic wastewater effluent loadings of various pollutants are identified through the following specific steps:

(1) With subdistricts as basic units for hotspot identification, sum up the annual domestic wastewater effluent loadings in each subdistrict; calculate the per area and per capita wastewater loading intensity in each subdistrict; and arrange the above three indicators in a descending order and then summarize them to identify the hotspot areas of domestic wastewater effluent loadings;

(2) For each subdistrict, sum up the domestic wastewater effluent loadings in each subdistrict on a single working day and rest day, respectively, and then compare temporal fluctuations to identify the hotspot periods of wastewater effluent loadings on a single working day and rest day, respectively.

Beneficial effects: The spatial and temporal feature-based method for measuring domestic wastewater effluent loadings provided by the present invention helps identify key pollution areas and periods, lays a methodological foundation for precision pollution control and may raise the spatial and temporal accuracy of the measurement of domestic wastewater effluent loadings, and discriminate "hotspots" of domestic wastewater effluent loadings, thereby leading the innovation in water environment treatment means and methods; and further, the calculation method of the present invention is flexible, convenient and highly universal. The data needed are also publicly available.

BRIEF DESCRIPTION OF THE DRAWINGS

FIG. 1 is a flowchart of a measuring method provided by the present invention.

DETAILED DESCRIPTION OF PREFERRED EMBODIMENTS

The technical solutions of the present invention will be described in detail below by referring to the accompanying drawings, but the scope of protection of the present invention is not limited to the embodiments.

Embodiment

Taking the measurement of domestic COD loading in a region of Wuxi City, Jiangsu Province in 2017 as an example, this region is adjacent to the Taihu Lake, has an area of about 500 km$^2$, covers three administrative districts and shows a high degree of urbanization. As shown in FIG. 1, the spatial and temporal feature-based method for measuring domestic wastewater effluent loadings in this embodiment comprises the following steps:

Step 1: Establish a model for measuring domestic wastewater COD production

Basic principle of the model for measuring domestic wastewater COD production: COD production=number of population×per capita daily consumption of domestic water×domestic wastewater effluent coefficient×COD concentration×number of days. In order to accurately identify COD production "hotspots", the target region is divided into grids with a resolution of 5 m×5 m, and each grid is independently calculated as a basic calculation unit.

The domestic wastewater COD production of grid k in a target year is measured by the following specific method:

$$Q_{k,w}=p \times w \times f \times C_{w,n} \times 10^{-9}$$

$$Q_{k,r}=p \times w \times f \times C_{r,n} \times 10^{-9}$$

$$Q_k=Q_{k,w} \times d_w + Q_{k,r} \times d_r$$

where:

$Q_{k,w}$ and $Q_{k,r}$ are the domestic wastewater COD production (t) of grid k on a single working day and a rest day, respectively; $Q_k$ is annual domestic wastewater COD production (t) of grid k; p is the number of population (person) of grid k; w is the per capita daily consumption of domestic water (L/person/day); f is the domestic wastewater effluent coefficient; $C_{w,n}$ and $C_{r,n}$ are the weighted average COD concentration (mg/L) of subdistrict n on working days and rest days, respectively; n is the subdistrict to which grid k belongs; $d_w$ and $d_r$ are the number of working days (day) and the number of rest days (day), respectively in a target year.

Step 2: calculate regional population distribution raster data (1) Download the latest China population data raster layer from Worldpop database (2015, resolution 100 m×100 m);

(2) In ArcGIS software, use a regional boundary vector layer to intercept the China population data raster layer in 2015 to obtain a regional population data raster layer in 2015 (resolution 100 m×100 m);

(3) According to the population data in 2017 and 2015 in a regional statistical yearbook, calculate the population conversion coefficient between the two years, which is 1.0065;
(4) Use the "Grid calculator" tool in ArcGIS software to multiply the regional population distribution raster layer in 2015 with the population conversion coefficient 1.0065 to obtain a regional population distribution raster layer in 2017 (resolution 100 m×100 m);
(5) Use the "Resampling" tool in ArcGIS software to downscale the regional population distribution raster layer in 2017 (100 m×100 m) to a regional population distribution raster layer in 2017 (5 m×5 m).

Step 3: Obtain a per capita COD production coefficient
(1) Obtain per capita daily consumption of domestic water and a wastewater production coefficient:

The per capita daily consumption of domestic water is data released in the work report of Wuxi Municipal Water Saving Office and the value is 137 L/person/day; and the wastewater production coefficient adopts the representative value of Wuxi in the literature and the value is 0.85;

(2) Monitor pollutant concentrations
a. Determination of monitoring points

This region consists of three administrative districts, including administrative district 1, administrative district 2 and administrative district 3. Among them, administrative district 1 is an economic, business and cultural center of the region, is densely populated and produces a large amount of domestic wastewater; administrative district 2 has concentrated high-tech enterprises, a low population density and a small amount of domestic wastewater production; and administrative district 3 has a large area, with dense rural distribution and is backward in industry.

According to the Division Codes for Statistics and Urban and Rural Division Codes in 2018 published by the National Bureau of Statistics, administrative district 1 completely belongs to urban division, so one urban quarter sample is selected in administrative district 1 as a representative quarter of this district; administrative district 2 and administrative district 3 both include urban division and suburban division, so one urban quarter sample and one suburban quarter sample are selected in administrative district 2 and administrative district 3 respectively as representative quarters of the administrative districts. To sum up, five quarters in total for field monitoring are determined in the region.

b. Field monitoring

The monitoring time starts from Friday 7:00 to Sunday 7:00, and samples are taken for consecutive 48 h at an interval of 4 h. The instantaneous flow is recorded. The samples are kept for subsequent analysis.

c. Monitoring record and detection method

Record the pipe network diameter, longitude and latitude of the wastewater discharge outlets of the quarters before sampling, record the wastewater flow at the moment during sampling each time, and set the sampling volume each time at 500 mL, i.e., the volume of a spring water bottle. Immediately send the samples to a laboratory, store them at 4° C., and use the national standard analytical method to detect COD concentrations in the samples.

d. Calculate the weighted average COD concentration of each sampling quarter on a single working day and a single rest day, respectively, by the following formulae:

$$c_{w,m} = \frac{\sum_{i=1}^{6}(q_{w,i} \times c_{w,i})}{\sum_{i=1}^{6} q_{w,i}}$$

$$c_{r,m} = \frac{\sum_{i=1}^{6}(q_{r,i} \times c_{r,i})}{\sum_{i=1}^{6} q_{r,i}}$$

where:
$c_{w,m}$ and $c_{r,m}$ are the weighted average COD concentration of sampling quarter m on working days and rest days, respectively (mg/L); i is the number of sampling intervals on a single working day or rest day; $q_{w,i}$ and $q_{r,i}$ are the wastewater flow in sampling interval i of working days and rest days, respectively (L/s); and $c_{w,i}$ and $c_{r,i}$ are the COD concentration in sampling interval i of working days and rest days, respectively (mg/L);

e. The weighted average COD concentration of domestic sources in each subdistrict on a single working day and that on a single rest day in the region are calculated by the following formulae:

$$C_{w,n} = \frac{N_a}{N_a + N_b + N_c} \times C_{w,c} + \frac{N_b}{N_a + N_b + N_c} \times C_{w,t} + \frac{N_c}{N_a + N_b + N_c} \times C_{w,r}$$

$$C_{r,n} = \frac{N_a}{N_a + N_b + N_c} \times C_{r,c} + \frac{N_b}{N_a + N_b + N_c} \times C_{r,t} + \frac{N_c}{N_a + N_b + N_c} \times C_{r,r}$$

where:
$C_{w,n}$ and $C_{r,n}$ are the weighted average COD concentration in subdistrict n on working days and rest days, respectively (mg/L); $N_a$ is the number of communities, which are under the jurisdiction of subdistrict n and are divided into urban codes; $N_b$ is the number of communities, which are under the jurisdiction of subdistrict n and are divided into suburban codes; $N_c$ is the number of communities, which are under the jurisdiction of subdistrict n and are divided into rural codes; $C_{w,n}$ and $C_{r,c}$ are the weighted average COD concentration in the urban quarters of subdistrict n on working days and rest days, respectively (mg/L); $C_{w,t}$ and $C_{r,t}$ are the weighted average COD concentration in the suburban quarters of subdistrict n on working days and rest days, respectively (mg/L); and $C_{w,r}$ and $C_{r,r}$ are the weighted average COD concentration in the rural quarters of subdistrict n on working days and rest days, respectively (mg/L);

f. Acquire a COD concentration distribution layer of each subdistrict in the region Sort the weighted average COD concentration of each subdistrict on working days and rest days, respectively into an Excel data form, use the "Connect" tool in ArcGIS to connect the "subdistrict" field in the data form same as that in the regional subdistrict vector diagram attribute, that is, add COD concentration information to the regional subdistrict vector diagram attribute, combine the information of the weighted average COD concentrations of domestic sources in each subdistrict in the region on working days and rest days with the vector diagram of the subdistrict to obtain a COD concentration distribution map of each subdistrict in the region.

Step 4: Calculate regional domestic wastewater COD production
(1) In ArcGIS software, use the "Element-to-grid" tool to convert the subdistrict vector layer that relates the COD concentration information into a raster layer, and set the resolution of the raster layer to be consistent with the resolution of the regional population distribution raster layer, i.e., 5 m×5 m;

(2) In ArcGIS software, use the "Grid calculator" tool to input the COD concentration spatial distribution layer of each subdistrict in the region, regional population distribution raster layer, per capita daily consumption of domestic water in 2017 and domestic wastewater effluent coefficient, multiply them with the number of working days, number of rest days and number of days in the whole year in 2017 respectively to obtain the domestic COD pollution loading distribution grid maps on the working days, on the rest days and in the whole year in 2017 respectively.

Step 5: Identify domestic COD production "hotspots" Domestic COD production "hotspots" include "hotspot" areas and "hotspot" periods.

(1) Identification of "hotspot" areas:

According to three indicators including annual domestic wastewater COD production, unit-area COD production intensity and per capita COD production intensity, subdistricts are sequenced based on the effluent loading condition. According to the orders under the three indicators, the top 10% of the subdistricts are defined as effluent loading "hotspot" areas.

(2) Identification of "hotspot" periods:

In ArcGIS software, use the "Form-displayed zone statistics" tool to conduct statistics on domestic wastewater COD production of each subdistrict on a single working day and a single rest day, respectively. Compare the domestic wastewater COD production on a single working day and a single rest day, respectively in each subdistrict and identify respective "hotspot" periods.

As described above, although the present invention has been expressed and presented with reference to specific preferred embodiments, these embodiments should not be interpreted as a limitation to the present invention. Various changes can be made in form and detail without departing from the spirit and scope of the present invention defined in the appended claims.

What is claimed is:

1. A spatial and temporal feature-based method that merges multi-source data for measuring one or more pollutants in domestic wastewater effluent loadings, for a specific region, wherein the method comprises the following steps:
   Step 1: establishing a spatial model for measuring regional domestic wastewater effluent loadings;
   Step 2: obtaining regional population distribution raster data according to open-source population distribution databases, statistical yearbooks and spatial analytical methods;
   Step 3: obtaining per capita effluent loading coefficients in the region based on field sampling and monitoring, and literature;
   Step 4: using the model, the regional population distribution raster data and the per capita effluent loading coefficients in the region to calculate regional domestic wastewater effluent loadings with geographic information system software; and
   Step 5: identifying hotspot periods and hotspot areas of domestic wastewater effluent loadings; and
   Step 6: based on identified hotspot periods and hotspot areas, performing source control and pollution reduction.

2. The method according to claim 1, wherein the pollutants are directly discharged from households and are selected from COD, $NH_3$—N, TN and TP.

3. The method according to claim 1, wherein at Step 1, the following calculation formulae are used to calculate the domestic wastewater effluent loadings on a single working day, on a single rest day and in a whole year, respectively:

$$Q_{k,w} = p \times w \times f \times C_{w,n} \times 10^{-9}$$

$$Q_{k,r} = p \times w \times f \times C_{r,n} \times 10^{-9}$$

$$Q_k = Q_{k,w} \times d_w + Q_{k,r} \times d_r$$

where:
   $Q_{k,w}$ and $Q_{k,r}$ are the domestic wastewater effluent loadings of grid k on a single working day and a single rest day, respectively, and the unit is ton; $Q_k$ is the domestic wastewater effluent loadings of grid k in a whole year, and the unit is ton; p is the population of grid k; w is the per capita daily consumption of domestic water, and the unit is L; f is the domestic wastewater effluent coefficient; $C_{w,n}$ and $C_{r,n}$ are the weighted average pollutant concentration of subdistrict n on working days and rest days, respectively, and the unit is mg/L; n is the subdistrict to which grid k belongs; and $d_w$ and $d_r$ are the number of working days and the number of rest days in a target year, respectively.

4. The method according to claim 3, wherein at Step 2, the regional population distribution raster data are obtained by the following method:
   (1) downloading a recently published regional population distribution data map of a specific historical year from the open-source databases;
   (2) using a regional administrative boundary layer to intercept a regional population distribution raster layer of the specific historical year to generate a regional population distribution map of the current year;
   (3) using the population data in the regional statistical yearbook to calculate a population conversion coefficient between a target year and the specific historical year, i.e., the population ratio between the two years;
   (4) in the geographic information system software, multiply the regional population distribution raster layer of the specific historical year with the population conversion coefficient to obtain a regional population distribution raster layer of the target year; and
   (5) in the geographic information system software, set a resolution of the regional population distribution raster layer.

5. The method according to claim 1, wherein at Step 3, the per capita effluent loading coefficients include a per capita daily consumption of domestic water, a domestic wastewater effluent coefficient and a concentration of various pollutants, wherein the per capita daily consumption of domestic water comes from regional statistical yearbooks or government work reports, and wherein the domestic wastewater effluent coefficient is obtained from existing literature, and the pollutant concentrations are obtained by means of field sampling and monitoring.

6. The method according to claim 1, wherein pollutant concentrations are monitored by the following specific method:
   (1) selecting representative residential quarters for monitoring by dividing a whole region into three categories including urban areas, suburban areas and rural areas; taking samples in each category, according to a subregional average housing price in a target year, uniformity in spatial distribution and field pre-investigation, determining residential quarters for actual monitoring, which can represent the communities or administrative villages to which they belong;

(2) monitoring the residential quarters-by choosing the general wastewater discharge outlet of each residential quarter as a sampling site to carry out monitoring; setting a sampling time to be on a working day and a rest day, and a sampling interval to be once every 4 hours;

(3) recording and storing the sample by recording a diameter of a wastewater discharge pipe and a longitude and latitude of the sampling site, recording a time that wastewater discharge needs to fill up a 3.5 L water bucket and calculating a wastewater flow; and applying standard analytical methods to store the samples and test the concentration of pollutants in samples;

(4) calculating a weighted average pollutant concentration of each sampling quarter on a single working day and rest day using the following formulae:

$$c_{w,m} = \frac{\sum_{i=1}^{6}(q_{w,i} \times c_{w,i})}{\sum_{i=1}^{6} q_{w,i}}$$

$$c_{r,m} = \frac{\sum_{i=1}^{6}(q_{r,i} \times c_{r,i})}{\sum_{i=1}^{6} q_{r,i}}$$

where:

$C_{w,m}$ and $c_{r,m}$ are the weighted average pollutant concentration of sampling quarter m on working days and rest days, respectively, and the unit is mg/L; i is the number of sampling intervals on a single working day or rest day; $q_{w,i}$ and $q_{r,i}$ are the wastewater flow in the sampling intervals of working days and rest days, respectively, and the unit is L/s; $c_{w,i}$ and $c_{r,i}$ are the pollutant concentration in the sampling intervals of working days and rest days, respectively, and the unit is mg/L;

(5) calculating the weighted average pollutant concentration of domestic wastewater in each subdistrict on a single working day and rest day, respectively by using the following formulae:

$$C_{w,n} = \frac{N_a}{N_a + N_b + N_c} \times C_{w,c} + \frac{N_b}{N_a + N_b + N_c} \times C_{w,t} + \frac{N_c}{N_a + N_b + N_c} \times C_{w,r}$$

$$C_{r,n} = \frac{N_a}{N_a + N_b + N_c} \times C_{r,c} + \frac{N_b}{N_a + N_b + N_c} \times C_{r,t} + \frac{N_c}{N_a + N_b + N_c} \times C_{r,r}$$

where:

$C_{w,n}$ and $C_{r,n}$ are the weighted average pollutant concentration in subdistrict n on working days and rest days, respectively, and the unit is mg/L; $N_a$ is the number of communities, which are under the jurisdiction of subdistrict n and are divided into urban codes; $N_b$ is the number of communities, which are under the jurisdiction of subdistrict n and are divided into suburban codes; $N_c$ is the number of communities, which are under the jurisdiction of subdistrict n and are divided into rural codes; $C_{w,c}$ and $C_{r,c}$ are the weighted average pollutant concentration in the urban quarters of subdistrict n on working days and rest days, respectively, and the unit is mg/L; $C_{w,t}$ and $C_{r,t}$ are the weighted average pollutant concentration in the suburban quarters of subdistrict n on working days and rest days, respectively, and the unit is mg/L; and $C_{w,r}$ and $C_{r,r}$ are the weighted average pollutant concentration in the rural quarters of subdistrict n on working days and rest days, respectively and the unit is mg/L; and (6) using geographic information system software to combine information of the weighted average pollutant concentrations of domestic sources in each subdistrict in a region on working days and rest days with a vector diagram of the subdistrict based on names of subdistricts to obtain a pollutant concentration distribution map of each subdistrict in the region.

7. The method according to claim 1, wherein at Step 4, the regional domestic wastewater effluent loadings are calculated through the following specific steps:

(1) using geographic information system software, converting a subdistrict vector layer that relates pollutant concentration information into a raster layer, and set setting a resolution of the raster layer to be consistent with the resolution of the regional population distribution raster layer;

(2) using geographic information system software, input a formula for calculating regional domestic wastewater effluent loadings, which is a product of the regional population distribution raster layer, the daily weighted average pollutant concentration distribution raster layer (subdistrict-specific), and other necessary parameters to obtain distribution maps of various pollutants on a single working day, on a single rest day and in a whole year.

8. The method according to claim 1, wherein at Step 5, hotspot periods and hotspot areas of domestic wastewater effluent loadings of various pollutants are identified through the following specific steps:

(1) summing up the annual domestic wastewater effluent loadings in each subdistrict; calculating a per area and per capita wastewater loading intensity in each subdistrict; and arranging the above three indicators in a descending order and then summarizing the three areas to identify the hotspot areas of domestic wastewater effluent loadings;

(2) summing up the domestic wastewater effluent loadings in each subdistrict on a single working day and rest day, and then comparing temporal fluctuations to identify the hotspot periods of wastewater effluent loadings on a single working day and rest day.

* * * * *